(12) United States Patent
Italiaie et al.

(10) Patent No.: US 11,679,003 B2
(45) Date of Patent: Jun. 20, 2023

(54) SURGICAL IMPLANT SYSTEM AND METHOD

(71) Applicant: WARSAW ORTHOPEDIC INC., Warsaw, IN (US)

(72) Inventors: Christel Italiaie, Memphis, TN (US); Mark R. Grizzard, Munford, TN (US); Matthew T. Marropode, Boulder, CO (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 190 days.

(21) Appl. No.: 17/217,316

(22) Filed: Mar. 30, 2021

(65) Prior Publication Data

US 2021/0212839 A1    Jul. 15, 2021

Related U.S. Application Data (63) Continuation of application No. 16/044,594, filed on Jul. 25, 2018, now Pat. No. 10,959,859.

(51) Int. Cl.
*A61F 2/46* (2006.01)
*A61F 2/30* (2006.01)
(Continued)

(52) U.S. Cl.
CPC ........ *A61F 2/4611* (2013.01); *A61B 17/7002* (2013.01); *A61B 17/7083* (2013.01);
(Continued)

(58) Field of Classification Search
CPC . A61B 17/70; A61B 17/7002; A61B 17/7083; A61B 17/7076; A61F 2/4611;
(Continued)

(56) References Cited

U.S. PATENT DOCUMENTS 8,137,356 B2 *   3/2012   Hestad ................. A61B 17/708
                                                              606/279
8,439,922 B1 *   5/2013   Arnold ................. A61B 17/708
                                                              606/279
(Continued)

FOREIGN PATENT DOCUMENTS

KR    10-2016-0134546 A    11/2016
WO       2005058386 A2     6/2005
(Continued)

OTHER PUBLICATIONS

International Searching Authority, ISA/KR, International Application Division, Korean Intellectual Property Office, 189 Cheongsa-ro, Seo•gu, Daejeon, 35208, Republic of Korea, International application No. PCT/US2019/042367, Date of mailing Oct. 31, 2019.
(Continued)

*Primary Examiner* — Jessica Weiss
(74) *Attorney, Agent, or Firm* — Sorell, Lenna & Schmidt, LLP (57) ABSTRACT

A surgical instrument comprises a first portion defining a cavity configured for disposal of a first implant support member. A second portion defines at least one passageway aligned with the cavity and including a guide engageable with a second implant support member to orient the second implant support member with the at least one passageway such that the second implant support member is connectable with the first implant support member. Systems, spinal constructs, spinal implants and methods are disclosed.

20 Claims, 8 Drawing Sheets

(51) Int. Cl.
*A61B 17/70* (2006.01)
*A61F 2/44* (2006.01)

(52) U.S. Cl.
CPC ...... *A61F 2/30771* (2013.01); *A61B 17/7076* (2013.01); *A61F 2/442* (2013.01); *A61F 2/4455* (2013.01); *A61F 2002/30772* (2013.01)

(58) Field of Classification Search
CPC .... A61F 2/30771; A61F 2/442; A61F 2/4455; A61F 2002/30772
USPC .................................. 606/99–100, 300–321
See application file for complete search history.

(56) References Cited

U.S. PATENT DOCUMENTS

| | | | | |
|---|---|---|---|---|
| 8,556,904 | B2* | 10/2013 | Rezach | A61B 17/7085 606/305 |
| 9,289,250 | B2* | 3/2016 | Wall | A61B 17/7079 |
| 9,408,716 | B1* | 8/2016 | Reitblat | A61B 17/7077 |
| 2008/0091213 | A1* | 4/2008 | Jackson | A61B 17/7085 606/151 |
| 2010/0114179 | A1* | 5/2010 | Moore | A61B 17/7085 606/86 A |
| 2013/0096635 | A1 | 4/2013 | Wall et al. | |
| 2013/0245705 | A1 | 9/2013 | McBride et al. | |
| 2014/0148865 | A1 | 5/2014 | Hennard et al. | |
| 2014/0277206 | A1* | 9/2014 | Reitblat | A61B 17/7091 606/86 A |
| 2015/0164569 | A1 | 6/2015 | Reitblat et al. | |
| 2015/0351810 | A1 | 12/2015 | Lindner et al. | |
| 2017/0164980 | A1 | 6/2017 | Le Roux et al. | |
| 2017/0238975 | A1 | 8/2017 | Doose et al. | |
| 2017/0348029 | A1 | 12/2017 | Asaad | |
| 2018/0092671 | A1* | 4/2018 | Krause | A61B 17/7085 |

FOREIGN PATENT DOCUMENTS

| | | |
|---|---|---|
| WO | 2007121271 A2 | 10/2007 |
| WO | 2009114422 A2 | 9/2009 |

OTHER PUBLICATIONS

PTO-892, U.S. Appl. No. 16/044,594, filed Jul. 23, 2020.
European Patent Office, 80298 Munich, Germany, Appl. 19839963.6, Extended European Search Report, dated Mar. 29, 2022.

* cited by examiner

SURGICAL IMPLANT SYSTEM AND METHOD

CROSS REFERENCE TO RELATED APPLICATIONS

This application is a continuation of U.S. patent application Ser. No. 16/044,594, filed Jul. 26, 2018, which is expressly incorporated by reference herein, in its entirety.

TECHNICAL FIELD

The present disclosure generally relates to medical devices for the treatment of musculoskeletal disorders, and more particularly to a spinal implant system and a method for treating a spine.

BACKGROUND

Spinal pathologies and disorders such as kyphosis, scoliosis and other curvature abnormalities, degenerative disc disease, disc herniation, osteoporosis, spondylolisthesis, stenosis, tumor and fracture may result from factors including trauma, disease and degenerative conditions caused by injury and aging. Spinal disorders typically result in symptoms including deformity, pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes correction, fusion, fixation, discectomy, laminectomy and implantable prosthetics. As part of these surgical treatments, spinal constructs such as vertebral rods are often used to provide stability to a treated region. Rods redirect stresses away from a damaged or defective region while healing takes place to restore proper alignment and generally support vertebral members. During surgical treatment, one or more rods and bone fasteners can be delivered to a surgical site. The rods may be attached via the fasteners to the exterior of two or more vertebral members. Surgical treatment may employ surgical instruments and implants that are manipulated for engagement with vertebrae to position and align one or more vertebrae. This disclosure describes an improvement over these prior technologies.

SUMMARY

In one embodiment, a surgical instrument is provided. The surgical instrument comprises a first portion defining a cavity configured for disposal of a first implant support member. A second portion defines at least one passageway aligned with the cavity and including a guide engageable with a second implant support member to orient the second implant support member with the at least one passageway such that the second implant support member is connectable with the first implant support member. In some embodiments, systems, spinal constructs, spinal implants and methods are disclosed.

In one embodiment, the surgical instrument includes a retainer defining a cavity configured for disposal of an extender cap and including at least one movable tab engageable with a mating surface of the extender cap. A plurality of longitudinal rails define a first axial slot and a second axial slot aligned with the cavity. At least one of the rails includes a guide engageable with extender tabs to orient the extender tabs with the slots such that the extender tabs are connectable with the extender cap.

In one embodiment, a spinal implant system is provided. The spinal implant system comprises a surgical instrument including a first portion defining a cavity and a second portion defining at least one passageway aligned with the cavity. The second portion includes a guide. An implant support includes a cap disposable with the first portion and extender tabs engageable with the guide to orient the extender tabs with the at least one passageway such that the extender tabs are connectable with the cap. A bone fastener receiver is engageable with the tabs.

BRIEF DESCRIPTION OF THE DRAWINGS

The present disclosure will become more readily apparent from the specific description accompanied by the following drawings, in which.

DETAILED DESCRIPTION

The exemplary embodiments of the surgical system and related methods of use disclosed are discussed in terms of medical devices for the treatment of musculoskeletal disorders and more particularly, in terms of a spinal implant system and a method for treating a spine. In some embodiments, the systems and methods of the present disclosure comprise medical devices including surgical instruments and implants that are employed with a surgical treatment, as described herein, for example, with a cervical, thoracic, lumbar and/or sacral region of a spine.

In some embodiments, the present surgical system comprises a surgical instrument configured to guide and/or align one or more components of an implant support, implant and/or spinal construct into engagement for connection and/or assembly of the components. In some embodiments, the surgical instrument includes a retaining chamber for an implant support member, for example, an extender cap. In some embodiments, the surgical instrument includes a guide to align an implant support member, for example, at least one extender tab with at least one axial passageway for connection with an extender cap. In some embodiments, the retaining chamber includes at least one movable tab, for example, spring tabs configured to create a friction fit with a cap of an implant support to retain the cap in the retaining chamber.

In some embodiments, the surgical instrument includes a guide engageable with at least one extender tab to guide and/or align the at least one extender tab into the at least one axial passageway, for example, axial slots. In some embodiments, the slots are configured to align the extender tabs with the retaining chamber for connection with an extender cap. In some embodiments, subsequent to assembly of one or more extender components such that the extender cap is connected with extender tabs, the surgical instrument includes a ramp guide engageable with the extender cap to guide disengagement of the assembled extender components from the surgical instrument. In some embodiments, the surgical instrument includes axial slots configured for disposal of the extender tabs to facilitate locking a screw assembly in a selected orientation and sliding the cap onto the extender tabs. In some embodiments, the present surgical system comprises a surgical instrument that avoids manually aligning extender tabs with an extender cap to attach the extender cap with the extender tabs.

In some embodiments, the present surgical system comprises a surgical instrument including an assembly device configured to guide and/or align extender tabs into engagement with an extender cap for connection and/or assembly of the components of an implant support including an extender. In some embodiments, the assembly device includes an extender cap reload instrument configured to reattach extender tabs with an extender cap.

In some embodiments, the present surgical system comprises a surgical instrument that is employed with a method including the step of sliding an extender cap into a retainer portion of the surgical instrument. In some embodiments, the method includes the step of retaining the extender cap in the retainer by one or more movable tabs. In some embodiments, the method includes the step of locating one or more arms of a bone screw extender. In some embodiments, the method includes the step of translating the surgical instrument along the extender arms. In some embodiments, the method includes the step of applying a downward force to the retainer of the surgical instrument such that the extender cap engages the arms. In some embodiments, engagement of the extender cap with the arms provides audible and/or tactile indicia. In some embodiments, the method includes the step of applying an upward force on the surgical instrument to disengage the extender cap from the retainer.

In some embodiments, the surgical system includes extender tabs. In some embodiments, the extender tabs are configured for aligning an implant, such as, for example, a bone fastener, with various instruments and providing an access path for set screws and rods. In some embodiments, the extender tabs are connectable with the bone fastener.

In some embodiments, the surgical system of the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. In some embodiments, the surgical system of the present disclosure may be employed with other osteal and bone related applications, including those associated with diagnostics and therapeutics. In some embodiments, the disclosed surgical system may be alternatively employed in a surgical treatment with a patient in a prone or supine position, and/or employ various surgical approaches to the spine, including anterior, posterior, posterior mid-line, direct lateral, postero-lateral, and/or antero-lateral approaches, and in other body regions. The surgical system of the present disclosure may also be alternatively employed with procedures for treating the lumbar, cervical, thoracic, sacral and pelvic regions of a spinal column. The surgical system of the present disclosure may also be used on animals, bone models and other non-living substrates, such as, for example, in training, testing and demonstration.

The surgical system of the present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. In some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

As used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, microdiscectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. In some embodiments, as used in the specification and including the appended claims, the term "tissue" includes soft tissue, ligaments, tendons, cartilage and/or bone unless specifically referred to otherwise.

The following discussion includes a description of a surgical system including a surgical instrument, related components and methods of employing the surgical system in accordance with the principles of the present disclosure. Alternate embodiments are also disclosed. Reference is made in detail to the exemplary embodiments of the present disclosure, which are illustrated in the accompanying figures. Turning to FIGS. 1-5, there are illustrated components of a surgical system, such as, for example, a spinal implant system 10.

The components of spinal implant system 10 can be fabricated from biologically acceptable materials suitable for medical applications, including metals, synthetic polymers, ceramics and bone material and/or their composites. For example, the components of spinal implant system 10, individually or collectively, can be fabricated from materials such as stainless steel alloys, aluminum, commercially pure titanium, titanium alloys, Grade 5 titanium, super-elastic titanium alloys, cobalt-chrome alloys, superelastic metallic alloys (e.g., Nitinol, super elasto-plastic metals, such as GUM METAL®), ceramics and composites thereof such as calcium phosphate (e.g., SKELITE™), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tricalcium phosphate (TCP), hydroxyapatite (HA)-TCP, calcium sulfate, or other resorbable polymers such as polyaetide, polyglycolide, polytyrosine carbonate, polycaroplaetohe and their combinations.

Various components of spinal implant system 10 may have material composites, including the above materials, to achieve various desired characteristics such as strength, rigidity, elasticity, compliance, biomechanical performance, durability and radiolucency or imaging preference. The components of spinal implant system 10, individually or collectively, may also be fabricated from a heterogeneous material such as a combination of two or more of the above-described materials. The components of spinal implant system 10 may be monolithically formed, integrally connected or include fastening elements and/or instruments, as described herein.

Spinal implant system 10 is employed, for example, with a fully open surgical procedure, a minimally invasive procedure including percutaneous techniques, and mini-open surgical techniques to deliver and introduce instrumentation and/or a spinal implant, such as, for example, a bone fastener, at a surgical site of a patient, which includes, for example, a spine. In some embodiments, the spinal implant can include one or more components of one or more spinal constructs, such as, for example, interbody devices, interbody cages, bone fasteners, spinal rods, tethers, connectors, plates and/or bone graft, and can be employed with various surgical procedures including surgical treatment of a cervical, thoracic, lumbar and/or sacral region of a spine.

Spinal implant system 10 includes a surgical instrument, such as, for example, a connector 12. Connector 12 is configured to guide and/or align an implant support member, such as, for example, extender tabs 152, 152a into engagement with an implant support member, such as, for example, an extender cap 22 for connection and/or assembly of the components of an extender connected with a bone fastener assembly 150. In some embodiments, connector 12 comprises an assembly device for attaching components of an implant support, for example, an extender and avoids the step of manually aligning extender tabs with an extender cap to attach the extender cap with the extender tabs. In some embodiments, connector 12 comprises an extender cap reload instrument configured to reattach extender tabs with an extender cap.

Connector 12 extends between an end 14 and an end 16. Connector 12 includes a portion, such as, for example, a retainer 20 disposed at end 14. Retainer 20 is configured for disposal of extender cap 22. Retainer 20 includes a wall 24. Wall 24 includes portions 24a, 24b, 24c and 24d. Wall 24 includes an inner surface 26 extending along portions 24a, 24b, 24c and 24d. Surface 26 defines a cavity 28 configured for disposal of cap 22. Cavity 28 includes a substantially rectangular configuration. In some embodiments, cavity 28 may have various configurations including, for example, round, oval, polygonal, irregular, consistent, variable, uniform and non-uniform.

Figures 6, 7, 8:
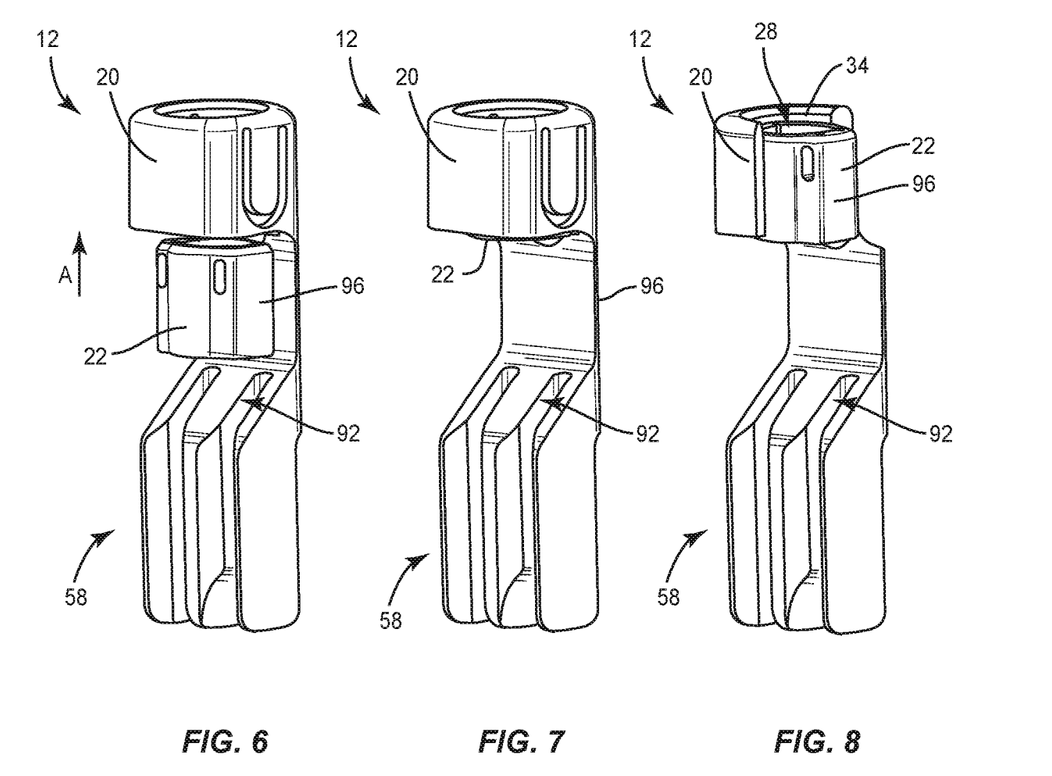
FIG. 6 is a perspective view of components of one embodiment of a surgical system in accordance with the principles of the present disclosure.
FIG. 7 is a perspective view of the components shown in FIG. 6.
FIG. 8 is a perspective view, in part cutaway, of the components shown in FIG. 6.

Portions 24a, 24b, 24c and 24d respectively meet at corners 30 along the inner surface of wall 24. In some embodiments, the inner surfaces of portions include an arcuate surface adjacent corners 30 to facilitate engagement with cap 22. Portions 24a, 24b, 24c, 24d and corners 30 are shaped such that a cross section of cavity 28 is configured for disposal of cap 22, as shown in FIG. 8. In some embodiments, corners 30 may have various configurations including, for example, irregular, consistent, variable, uniform and non-uniform. Corners 30 extend axially along wall 24. In some embodiments, corners 30 extend at alternate orientations along wall 24, such as, for example, at transverse, perpendicular and/or other angular orientations such as acute or obtuse, and/or may be offset or staggered.

Figure 5:
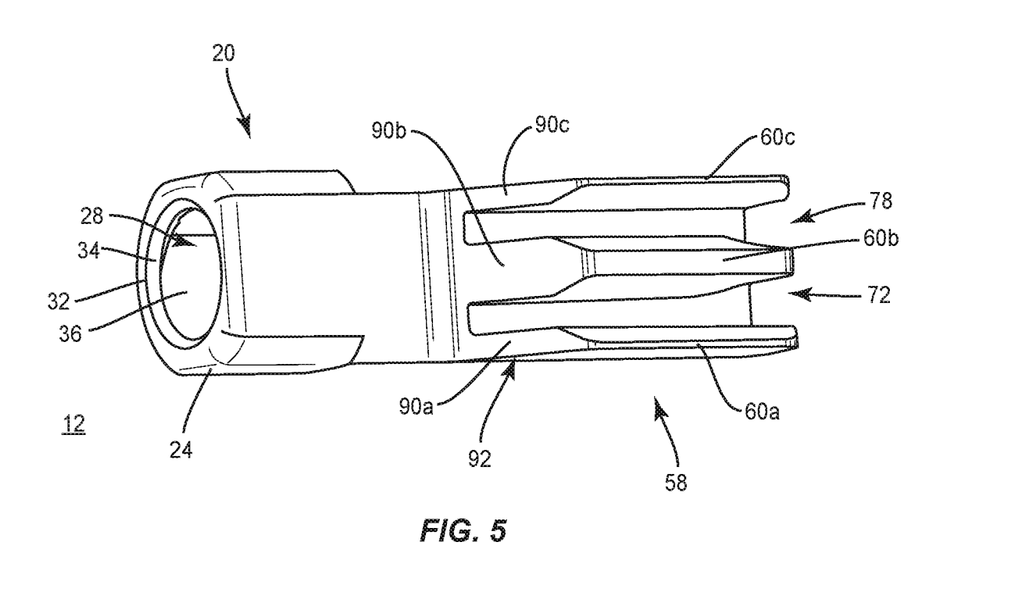
FIG. 5 is a perspective view of the components shown in FIG. 2.

Wall 24 includes a surface 32 that defines a flange 34. Flange 34 is disposed about an opening 36 of cavity 28, as shown in FIG. 5. Flange 34 is configured to abut cap 22 to retain cap 22 within cavity 28. For example, as extender tabs 152, 152a translate into engagement with cap 22, flange 34 resists and/or prevents extender tabs 152, 152a from forcing cap 22 out of cavity 28.

Figure 1:
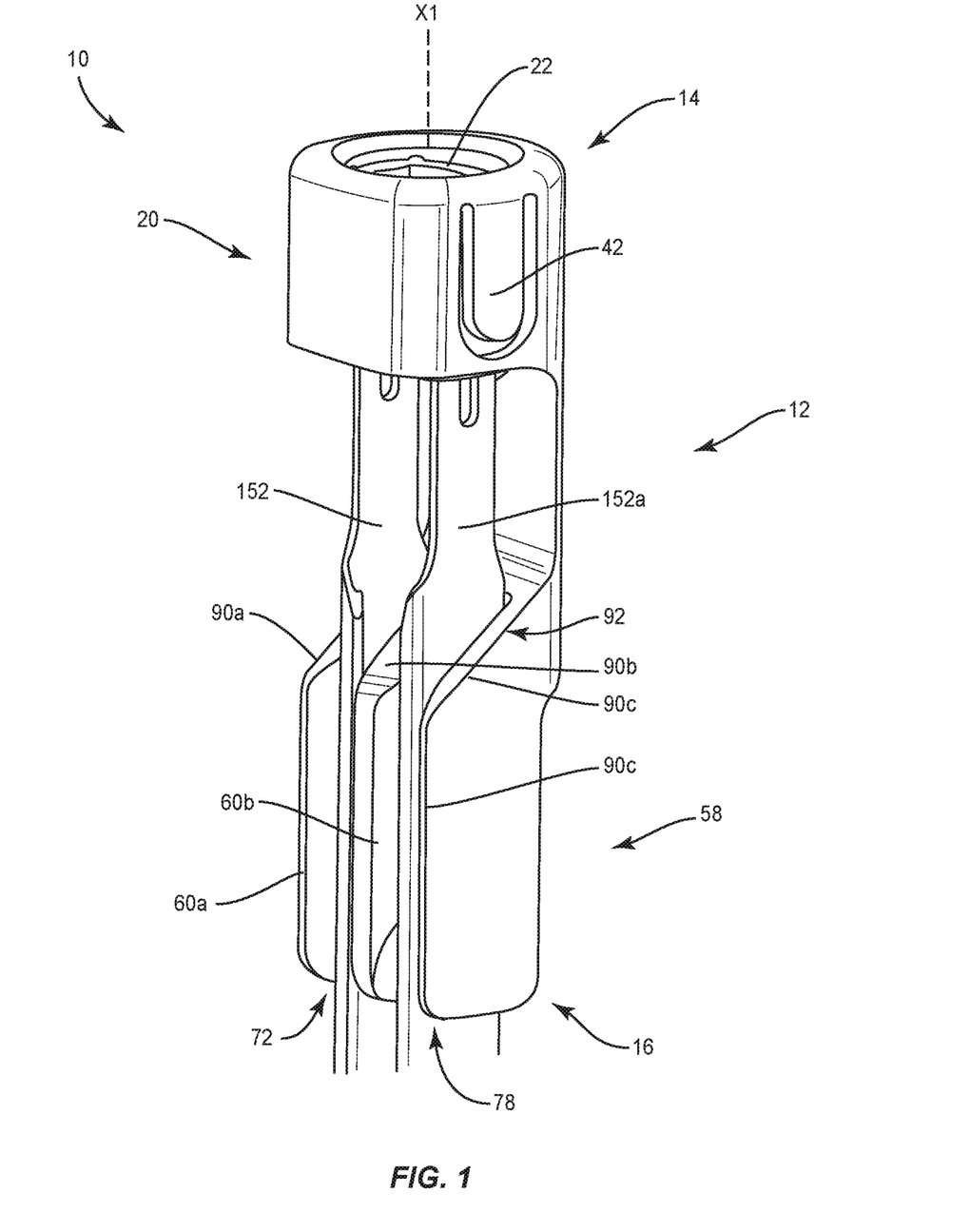
FIG. 1 is a perspective view of components of one embodiment of a surgical system in accordance with the principles of the present disclosure.
Figure 2:
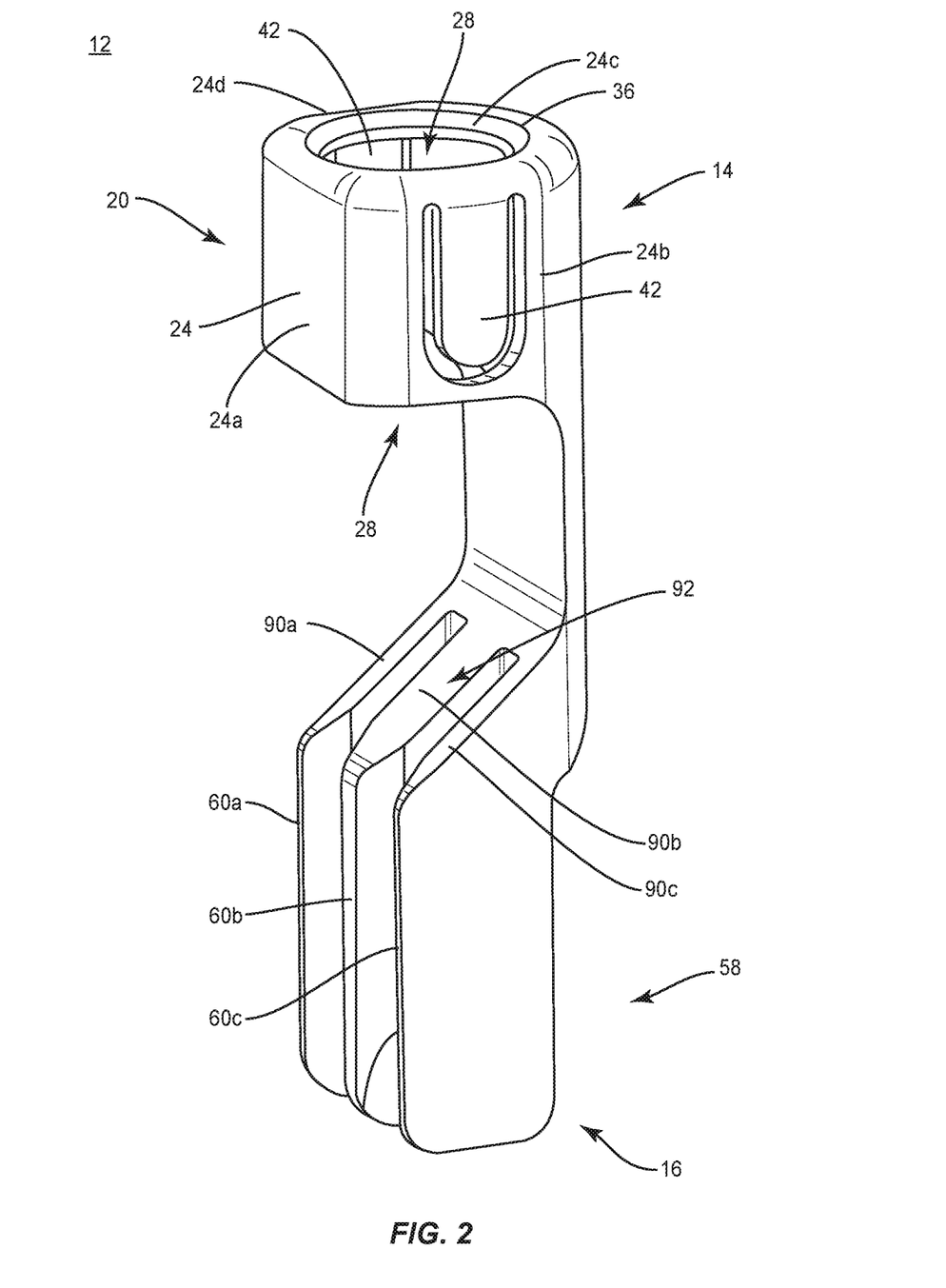
FIG. 2 is a perspective view of components of one embodiment of a surgical system in accordance with the principles of the present disclosure.
Figure 3:
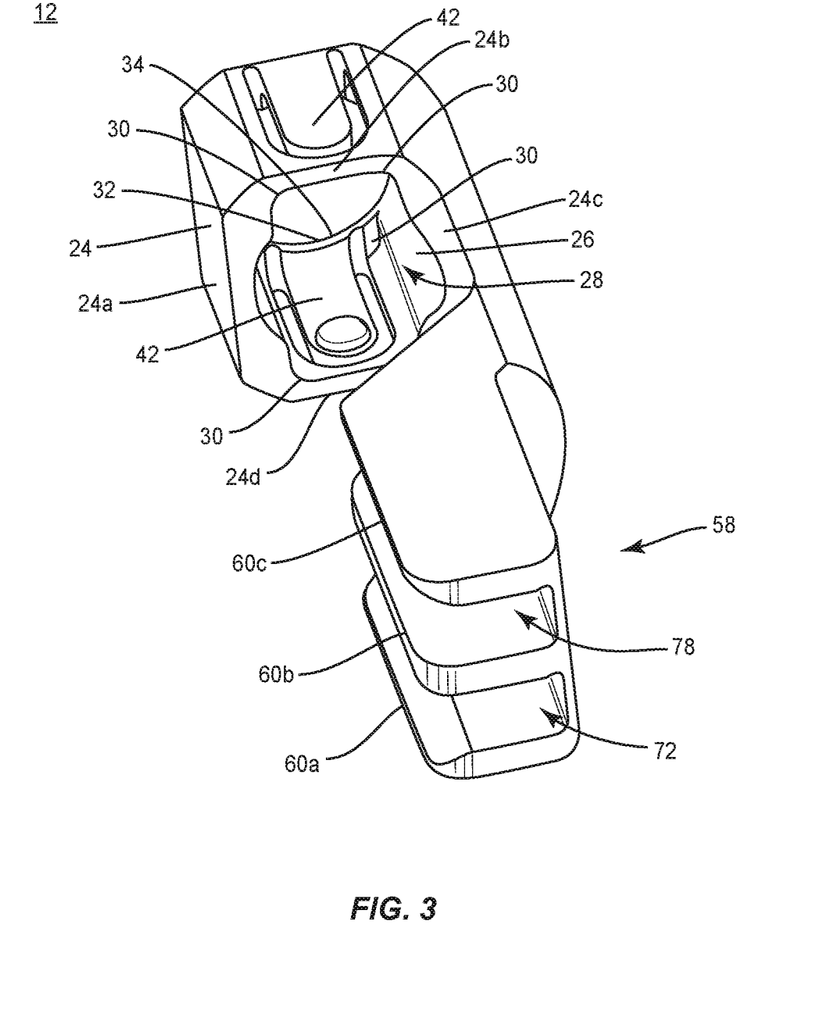
FIG. 3 is a perspective view of the components shown in FIG. 2.
Figure 4:
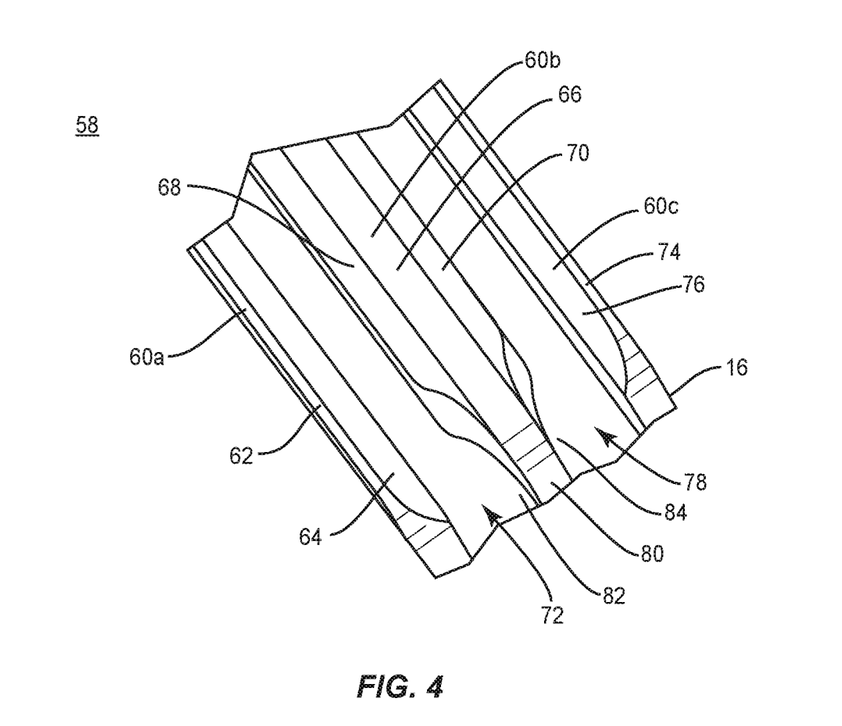
FIG. 4 is a break away view of the components shown in FIG. 2.

Walls 24a and 24d include tabs 42. Tabs 42 are movable to resist and/or prevent axial translation of cap 22, which facilitates attachment of a cap 22 to extender tabs 152, 152a, as described herein. Tabs 42 are disposed in alignment with wall 24. Tabs 42 are disposed on opposing sides of cavity 28 with walls 24a and 24d, as shown in FIG. 3. Tabs 42 extend within walls 24a, 24d and include an inward spring and/or resilient bias upon engagement with cap 22 to facilitate a friction fit with cap 22. Tabs 42 include a surface 44 configured to frictionally engage a mating surface of cap 22, as described herein. In some embodiments, tabs 42 are configured as cantilever arms that extend along a portion of wall 24. In some embodiments, wall 24 includes one or a plurality of tabs disposed with one or more portions 24a, 24b, 24c, 24d. In some embodiments, tabs 42 are disposed at alternate orientations relative to wall 24, such as, for example, at transverse, perpendicular and/or other angular orientations such as acute or obtuse, and/or may be offset or staggered.

Connector 12 includes a guide 58 defining an axis X1. Guide 58 includes longitudinal rails 60a, 60b and 60c extending along axis X1. Rail 60a includes a wall 62 having a surface 64. Rail 60b includes a wall 66 having a surface 68 and a surface 70. Surfaces 64, 68 define a passageway, such as, for example, an axial slot 72. Slot 72 extends along axis X1. Slot 72 is disposed in alignment with cavity 28 to facilitate engagement of extender tab 152 with cap 22, as described herein. Surfaces 64, 68 are disposed at an angle relative to axis X1. In some embodiments, all or only a portion of surfaces 64, 68 may have alternate configurations, such as, for example, irregular, uniform, non-uniform, offset, staggered, tapered, arcuate or undulating. Surfaces 64, 68 direct and/or guide insertion of extender tab 152 into slot 72. In some embodiments, guide 58 is monolithically formed with retainer 20. In some embodiments, guide 58 is permanently fixed relative to retainer 20.

Rail 60c includes a wall 74 having a surface 76. Surfaces 70, 76 define a passageway, such as, for example, an axial slot 78. Slot 78 extends along axis X1. Slot 78 is disposed in alignment with cavity 28 to facilitate engagement of extender tab 152a with cap 22, as described herein. Surfaces 70, 76 are disposed at an angle relative to axis X1. In some embodiments, all or only a portion of surfaces 70, 76 may have alternate configurations, such as, for example, irregular, uniform, non-uniform, offset, staggered, tapered, arcuate or undulating. Surfaces 70, 76 direct and/or guide insertion of extender tab 152a into slot 78. In some embodiments, slots 72, 78 are permanently fixed relative to cavity 28.

Slots 72, 78 are configured to position extender tabs 152, 152a to lock bone fastener 100 in a correct orientation to facilitate connection with cap 22. Slots 72, 78 are configured to guide and/or direct extender tabs 152, 152a into engagement with cap 22 disposed with retainer 20.

Figures 9, 10:
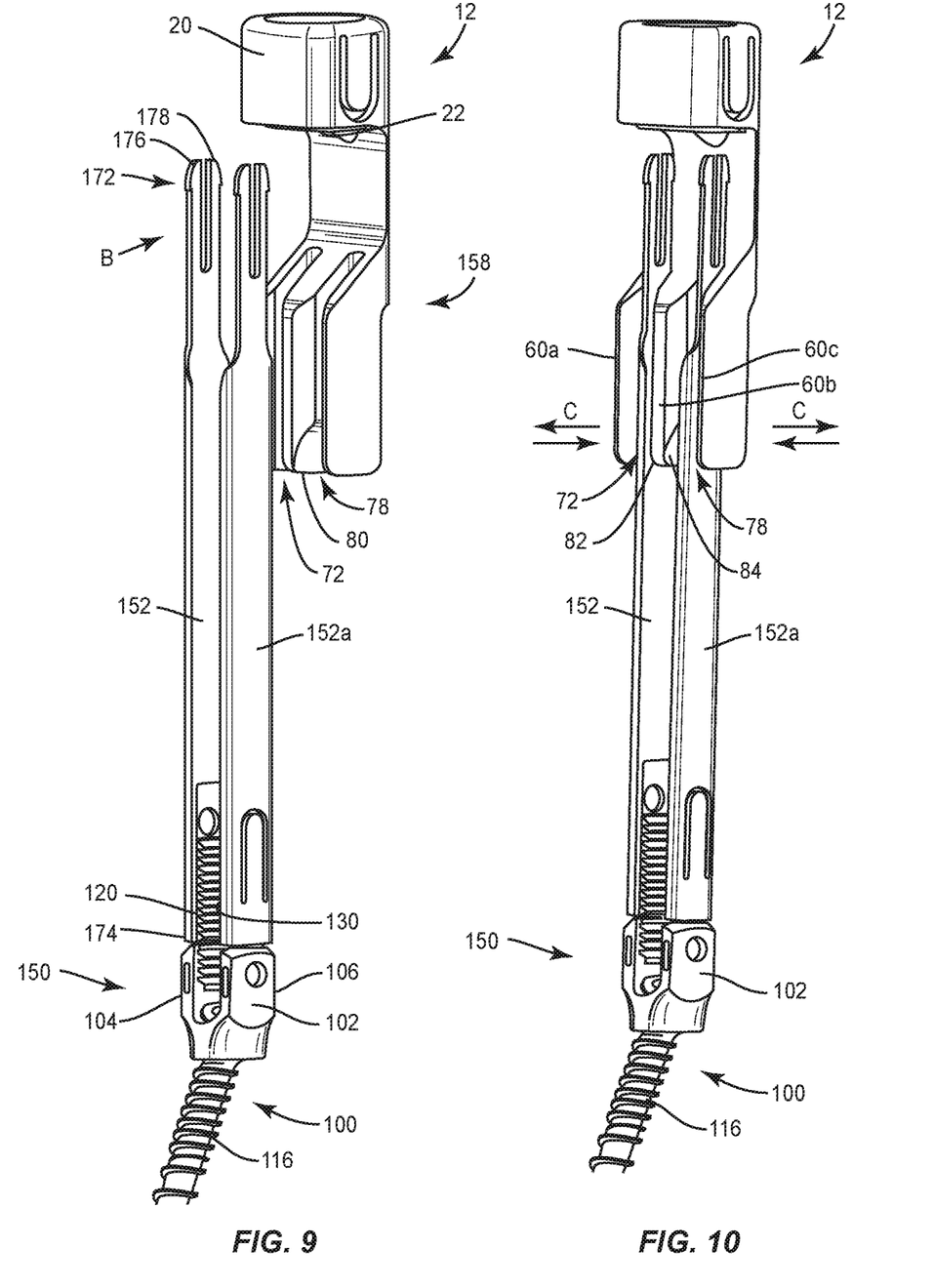
FIG. 9 is a perspective view of components of one embodiment of a surgical system in accordance with the principles of the present disclosure.
FIG. 10 is a perspective view of the components shown in FIG. 9.

Rail 60b comprises a central rail disposed between rails 60a, 60c such that slots 72, 78 are bifurcated. Rail 60b includes a tapered surface 80 disposed at end 16. Surface 80 includes a surface 82 disposed in communication with surface 68. Surface 82 is tapered such that surface 82 decreases along surface 80 from surface 68 to end 16. Surface 80 includes a surface 84 disposed in communication with surface 70. Surface 84 is tapered such that surface 84 decreases along surface 80 from surface 70 to end 16. Surfaces 82, 84 are configured to splay extender tabs 152, 152a upon engagement of extender tabs 152, 152a with connector 12, as shown in FIG. 10. Extender tabs 152, 152a slide and/or translate along surfaces 82, 84. Guide 58 directs and/or aligns extender tabs 152, 152a for disposal into slots 72, 78 to facilitate alignment of extender tabs 152, 152a with cap 22.

Rails 60a, 60b, 60c include a proximal surface 90a, 90b, 90c, respectively, as shown in FIG. 5. Surfaces 90a, 90b, 90c are relatively disposed within a plane such that 90a, 90b, 90c comprise a planar surface engageable with cap 22. In some embodiments, all or only a portion of surfaces 90a, 90b, 90c may have alternate surface configurations, such as, for example, angled, irregular, uniform, non-uniform, offset, staggered, tapered, arcuate, undulating, mesh, porous, semi-porous, dimpled, pointed and/or textured.

Surfaces 90a, 90b, 90c define a guide, for example, a ramp 92. Surfaces 90a, 90b, 90c are disposed at an angle relative to axis X1 to define ramp 92. In some embodiments, ramp 92 is disposed at alternate orientations relative to axis X1, such as, for example, at transverse, perpendicular and/or other angular orientations such as acute or obtuse, and/or may be offset or staggered. Ramp 92 is selectively inclined to facilitate translation and/or disengagement of cap 22 from retainer 20 during removal of bone fastener assembly 150 from connector 12. For example, sliding of cap 22 along ramp 92 resists and/or prevents any force from an upward motion of connector 12 during disengagement from being applied to cap 22 thereby maintaining the connection of cap 22 with extender tabs 152, 152a, as described herein.

Cap 22 includes an inner surface (not shown) that defines a plurality of grooves. The grooves define channels configured for disposal of extender tabs 152, 152a. The inner surface is configured to provide audible and/or tactile indicia, such as, for example, an audible click indicating engagement of extender tabs 152, 152a with cap 22. Cap 22 includes an outer mating surface 96 configured for engagement with tabs 42 to retain cap 22 within cavity 28.

In various embodiments, cap 22 includes a guide section, serving function like guide 58. In this case, connector 12 is not needed, because this cap, having a guide section, is self-connecting, or self-guided. The guide section includes slots, which can in any manner disclosed herein be like slots 72, 78 of connector 12. It is contemplated that such slots could be shorter than slots 72, 78 shown for connector 12, such that the cap of these embodiments would not be markedly longer than cap 22 as shown.

Bone fastener assembly 150 includes a bone fastener 100. Bone fastener 100 includes a receiver 102. Receiver 102 is connected with extender tabs 152, 152a that extend along axis X1 and are disposed with connector 12, as described herein. Receiver 102 includes a pair of spaced apart arms 104, 106 that define an implant cavity configured for disposal of a component of a spinal construct, such as, for example, a spinal rod (not shown). Receiver 102 includes a socket configured for engagement with a surgical instrument. Receiver 102 includes an inner surface having a thread form located adjacent arm 104 and a thread form located adjacent arm 106. The thread forms of arms 104, 106 are configured for engagement with a coupling member. Bone fastener 100 includes a threaded shaft 116. Shaft 116 is configured to penetrate tissue, such as, for example, bone.

Arm 104 includes a break away tab 120 that is frangibly connected to arm 104 such that manipulation of tab 120 relative to arm 104 can fracture and separate tab 120 from arm 104 at a predetermined force and/or torque limit, as described herein. Arm 106 includes a break away tab 130 that is frangibly connected to arm 106 such that manipulation of tab 130 relative to arm 106 can fracture and separate tab 130 from arm 106 at a predetermined force and/or torque limit, as described herein. In some embodiments, as force and/or torque is applied to tabs 120, 130 and resistance increases, for example, the predetermined torque and force limit is approached.

In some embodiments, tabs 120, 130 can fracture and separate at a predetermined force or torque limit, which may be in a range of approximately 2 Newton meters (N-m) to 8 N-m. In some embodiments, tabs 120, 130 and arms 104, 106 may have the same or alternate cross section configurations, may be fabricated from a homogenous material or heterogeneously fabricated from different materials, and/or alternately formed of a material having a greater degree, characteristic or attribute of plastic deformability, frangible property and/or break away quality to facilitate fracture and separation of tabs 120, 130.

Bone fastener assembly 150 includes extender tabs 152, 152a connected with bone fastener 100. Extender tabs 152, 152a extend between a proximal end 172 and a distal end 174. Proximal end 172 includes spring tips 176, 178, as shown in FIG. 9. Spring tips 176, 178 are attachable with cap 22. The inner surface of cap 22 includes mating elements engageable with spring tips 176, 178 to resist and/or prevent disengagement of spring tips 176, 178, as described herein. Distal ends 174 are configured for slidable disposal of a portion of bone fastener 100, such as, for example, tabs 120, 130. In some embodiments, tabs 120, 130 are configured to releasably fix extender tabs 152, 152a with bone fastener 100. In some embodiments, extender tabs 152, 152a are each monolithically formed.

In various embodiments, connector 12 can be used to load multiple caps 22 to respective pairs of extender tabs 152 in succession. Benefits include saving time, and limiting motion of a surgeon or robot, during the procedure. Two sets of extender tabs 152 can be positioned adjacent each other, for instance, and the same connector 12 can be used to, first, (i) align a first pair of extender tabs 152 with a first of the caps 22, for connection between first tabs 152 and first cap 22, and, then, (ii) align a second pair of extender tabs 152 with a second of caps 22, for connection between second tabs 152 and second cap 22. In operation, the two sets of extender tab 152 can be adjacent each other, and connector 12 moved, laterally, or otherwise as needed, from first extender tab 152/cap 22 arrangement after alignment and connecting this first arrangement to second extender tab 152/cap 22 arrangement after alignment and connecting this second arrangement. The movement can include rotating connector 12, such as by about 180 degrees, if first extender tabs 152 are behind, or back-to-back, with second extender tabs 152. While rapid loading of two caps is mentioned by the examples above, any numbers of caps can be rapidly loaded in these ways. Three or four caps 22 can be rapidly loaded, for instance, by positioning the three or four pair of extender tabs 152 adjacent to each other, and operating connector 12 accordingly, to align a first of the pairs of extender tabs 152 and connect those tabs 152 to a first cap, then move quickly (by rotation and/or more linear movement, for instance) to align/connect a second of the pairs of extender tabs 152 with a second cap 22, then move quickly to align/connect a third of the pairs of extender tabs 152 with a third cap 22, and so on.

In assembly, operation and use, spinal implant system 10, similar to the systems and methods described herein, is employed with a surgical procedure, such as, for example, a treatment of an applicable condition or injury of an affected section of a spinal column and adjacent areas within a body. In some embodiments, one or all of the components of spinal implant system 10 can be delivered or utilized as a pre-assembled device or can be assembled in situ. Spinal implant system 10 may be completely or partially revised, removed or replaced.

In use, to treat vertebrae (not shown), a medical practitioner obtains access to a surgical site in any appropriate manner, such as through incision and retraction of tissues. In some embodiments, spinal implant system 10 can be used in any existing surgical method or technique including open surgery, mini-open surgery, minimally invasive surgery and percutaneous surgical implantation, whereby the vertebrae is accessed through a mini-incision, or sleeve that provides a protected passageway to the area. Once access to the surgical site is obtained, the particular surgical procedure can be performed for treating the spine disorder.

An incision is made in the body of a patient and a cutting instrument (not shown) creates a surgical pathway for implantation of components of spinal implant system 10. A preparation instrument (not shown) can be employed to prepare tissue surfaces of the vertebrae as well as for aspiration and irrigation of a surgical region.

Pilot holes (not shown) are made in selected levels of vertebrae for receiving shafts 116 of bone fastener assemblies 150. A surgical instrument, such as, for example, a driver is connected with bone fastener 100 and bone fasteners 100 are engaged with vertebrae. Extender tabs 152, 152a are connected with bone fasteners 100, as described herein. Cap 22 is disposed with retainer 20 of connector 12. Cap 22 is inserted into cavity 28, as shown by arrow A in FIG. 6. Surface 96 engages tabs 42 such that tabs 42 splay outwardly. The inward resilient bias of tabs 42, as shown in FIG. 7, cause tabs 42 to frictionally engage surface 96 to capture cap 22 with retainer 20.

Extender tabs 152, 152a are positioned adjacent connector 12, as shown in FIG. 9. Extender tabs 152, 152a are aligned with slots 72, 78. Extender tabs 152, 152a are laterally translated and guided into slots 72, 78 along surfaces 64, 68, 70, 76, as shown by arrow B in FIG. 9. Surfaces 64, 68, 70, 76 guide, which includes directing, aligning, contracting and/or splaying extender tabs 152, 152a into slots 72, 78, as shown by arrows C in FIG. 10. In some embodiments, extender tabs 152, 152a are axially translated and guided into slots 72, 78 along surfaces 82, 84, such that surfaces 82, 84 guide, which includes directing, aligning, contracting and/or splaying extender tabs 152, 152a into slots 72, 78. Positioning of extender tabs 152, 152a within slots 72, 78 aligns extender tabs 152, 152a with cap 22 to facilitate connection and/or assembly of the components of an extender including extender tabs 152, 152a/cap 22, which is connected with bone fastener assembly 150. In some embodiments, extender tabs 152, 152 are positioned within slots 72, 78 to connect extender tabs 152, 152a with cap 22 such that connector 12 comprises an extender cap reload instrument configured to reattach extender tabs 152, 152a with cap 22.

Figure 11:
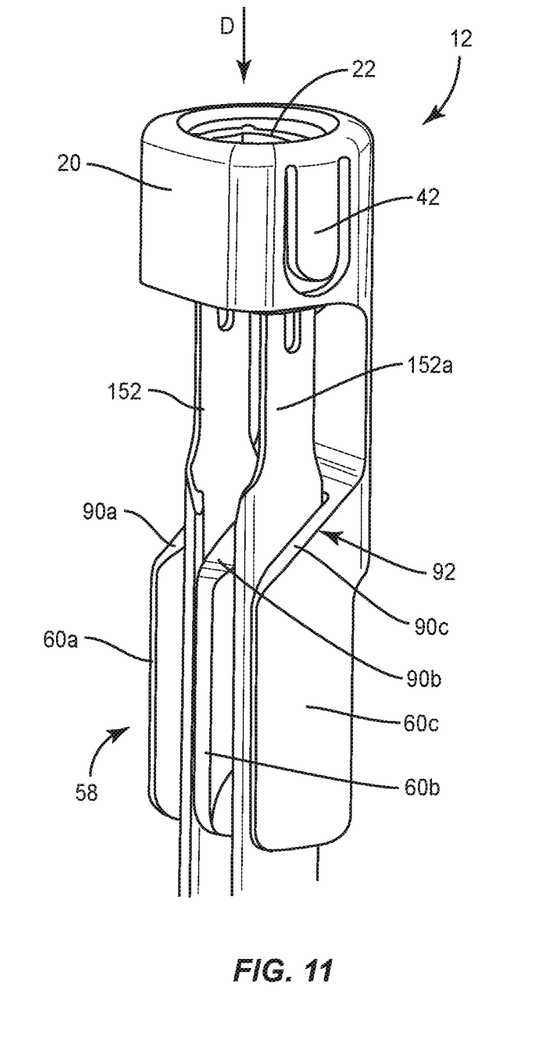
FIG. 11 is a break away view of the components shown in FIG. 9.

Bone fastener assembly 150 is held fixed and a downward force, as shown by arrow D in FIG. 11, is applied to retainer 20. Extender tabs 152, 152a are translated along slots 72, 78 into engagement with cap 22. Spring tips 176, 178 engage the mating elements of cap 22 and an audible and/or tactile indicia, such as, for example, a click indicates engagement of extender tabs 152, 152a with the inner surface of cap 22. Flange 34 resists and/or prevents disengagement of cap 22 from cavity 28 during insertion of extender tabs 152, 152a.

Figure 12:
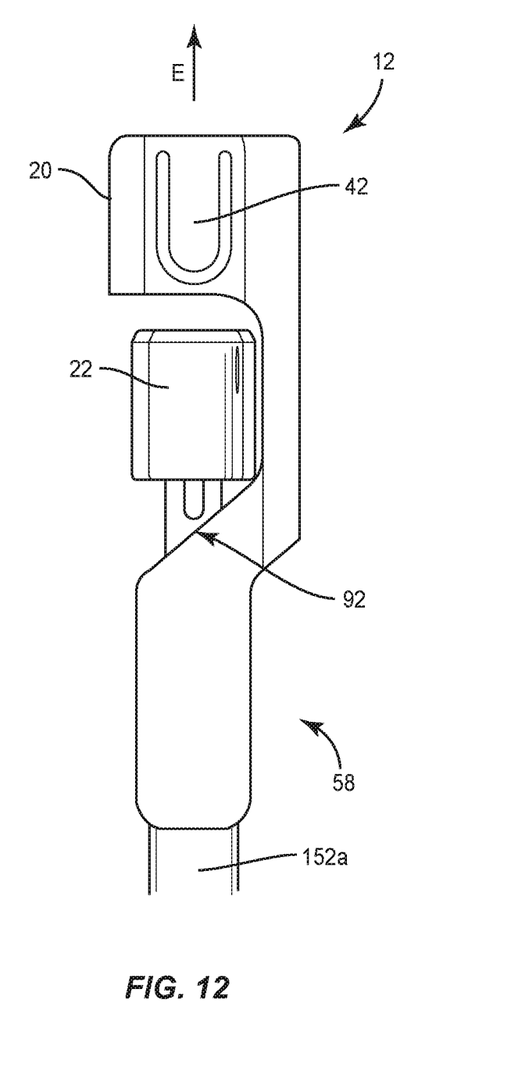
FIG. 12 is a side view of the components shown in FIG. 11.
Figure 13:
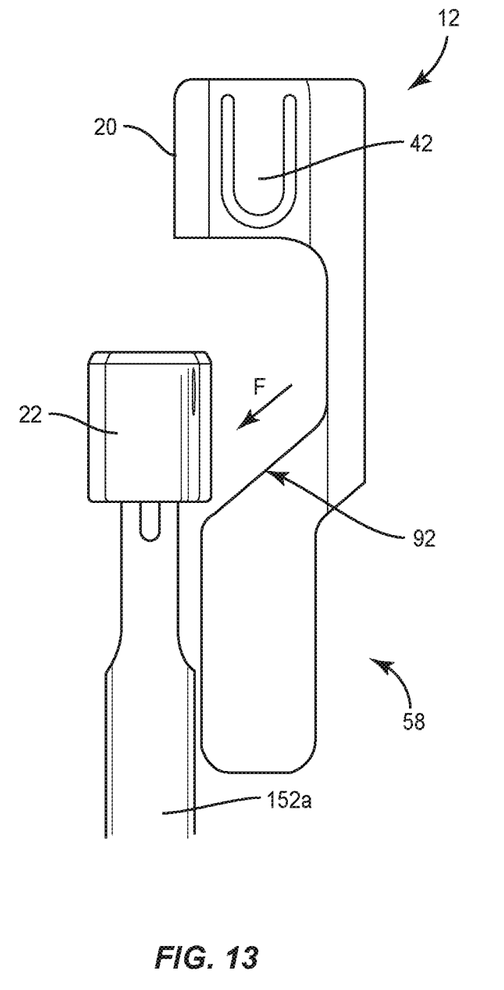
FIG. 13 is a side view of the components shown in FIG. 11.
Figure 14:
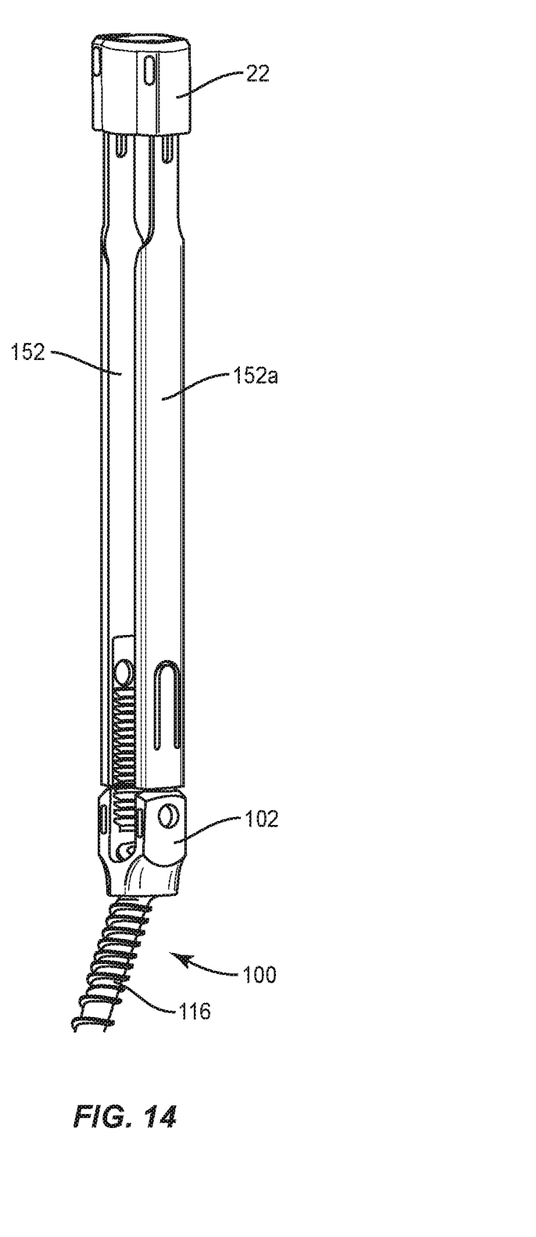
FIG. 14 is a perspective view of components of one embodiment of a surgical system in accordance with the principles of the present disclosure.

Bone fastener assembly 150 is held fixed and connector 12 is translated axially, as shown by arrow E in FIG. 12, to disengage bone fastener assembly 150 with the extender components attached to bone fastener 100 from connector 12. The frictional engagement of cap 22 with retainer 20 is overcome and surface 96 is released from tabs 42. Cap 22 is disengaged from retainer 20. As extender tabs 152, 152a are translated, cap 22 slidably engages ramp 92, in the direction of arrow F shown in FIG. 13, to facilitate disengagement of cap 22 from retainer 20 during removal of bone fastener assembly 150 from connector 12. Cap 22 is connected with bone screw assembly 150, as shown in FIG. 14.

In some embodiments, the surgical procedure includes delivering a spinal rod along the surgical pathway for connection with one or more bone fasteners 100. A reduction instrument (not shown) engages the spinal rod for reduction with receivers 102 and fixed thereto. In some embodiments, a tab breaker is engaged with extender tabs 152, 152a and is manipulated to apply a force to extender tabs 152, 152a and/or tabs 120, 130. As the force applied reaches a selected torque limit, the tab breaker breaks off extender tabs 152, 152a and/or tabs 120, 130 from bone fasteners 100.

Upon completion of a procedure, as described herein, the surgical instruments, assemblies and non-implanted components of spinal implant system 10 are removed and the incision(s) are closed. One or more of the components of spinal implant system 10 can be made of radiolucent materials such as polymers. Radiomarkers may be included for identification under x-ray, fluoroscopy, CT or other imaging techniques. In some embodiments, spinal implant system 10 may include one or a plurality of spinal rods, plates, connectors and/or bone fasteners for use with a single vertebral level or a plurality of vertebral levels.

In some embodiments, one or more bone fasteners, as described herein, may be engaged with tissue in various orientations, such as, for example, series, parallel, offset, staggered and/or alternate vertebral levels. In some embodiments, the bone fasteners may comprise multi-axial screws, sagittal adjusting screws, pedicle screws, mono-axial screws, uni-planar screws, facet screws, fixed screws, tissue penetrating screws, conventional screws, expanding screws, wedges, anchors, buttons, clips, snaps, friction fittings, compressive fittings, expanding rivets, staples, nails, adhesives, posts, fixation plates and/or posts.

In one embodiment, spinal implant system 10 includes an agent, which may be disposed, packed, coated or layered within, on or about the components and/or surfaces of spinal implant system 10. In some embodiments, the agent may include bone growth promoting material, such as, for example, bone graft to enhance fixation of the components and/or surfaces of spinal implant system 10 with vertebrae. In some embodiments, the agent may include one or a plurality of therapeutic agents and/or pharmacological agents for release, including sustained release, to treat, for example, pain, inflammation and degeneration.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A surgical instrument comprising:
    a first portion defining a cavity configured for disposal of a first implant support member, the cavity defining a longitudinal axis; and
    a second portion including spaced apart first and second axial slots, the slots each being offset from the longitudinal axis, the second portion being engageable with a second implant support member to orient the second implant support member with the slots such that the second implant support member is connectable with the first implant support member,
    wherein the first portion includes a body, the body including opposite proximal and distal walls and a side wall connecting the proximal wall to the distal wall, a cutout in the side wall defining a tab, the tab being movable relative to the side wall to prevent axial translation of the first implant support member, and
    wherein the tab is positioned entirely between the proximal and distal walls.

2. The surgical instrument recited in claim 1, further comprising the first implant support member and the second implant support member, wherein the first implant support member includes a cap and the second implant support member includes a pair of extender tabs configured for attachment with the cap.

3. The surgical instrument recited in claim 2, wherein the extender tabs each include opposite proximal and distal ends, the distal ends each being configured for engagement with a bone screw receiver, the proximal ends each including spaced apart tips attachable with the cap.

4. The surgical instrument recited in claim 3, further comprising the bone screw receiver.

5. The surgical instrument recited in claim 4, further comprising a bone screw shaft rotatably coupled to the bone screw receiver.

6. The surgical instrument recited in claim 2, wherein the extender tabs are each monolithically formed.

7. The surgical instrument recited in claim 1, wherein the second portion is monolithically formed with the first portion.

8. The surgical instrument recited in claim 1, wherein the cutout is a first cutout and the tab is a first tab, the side wall defining a second cutout opposite the first cutout, the second cutout defining a second tab.

9. The surgical instrument recited in claim 8, wherein the tabs are each positioned entirely between the proximal and distal walls.

10. The surgical instrument recited in claim 1, wherein the body comprises a circular bore extending through the proximal wall, the bore being in communication with the cavity.

11. The surgical instrument recited in claim 1, wherein the second portion includes a central rail and outer rails, the central and outer rails defining the slots.

12. The surgical instrument recited in claim 11, wherein the longitudinal axis intersects the central rail.

13. The surgical instrument recited in claim 11, wherein the central rail is positioned between the outer rails.

14. The surgical instrument recited in claim 1, wherein a distal end of the first portion is coupled to a proximal end of the second portion.

15. The surgical instrument recited in claim 1, wherein the first portion is permanently fixed relative to the second portion.

16. The surgical instrument recited in claim 1, wherein a position of the cavity is permanently fixed relative to positions of the slots.

17. A surgical instrument comprising:
    a first portion defining a cavity defining a longitudinal axis;
    a cap disposed in the cavity;
    a second portion including spaced apart first and second axial slots, the slots each being offset from the longitudinal axis, the second portion being monolithically formed with the first portion;
    a first extender positioned in the first slot such that a proximal end of the first extender is connected to the cap; and
    a second extender positioned in the second slot such that a proximal end of the second extender is connected to the cap,
    wherein the first portion includes a body, the body including opposite proximal and distal walls and a side wall connecting the proximal wall to the distal wall, a cutout in the side wall defining a tab, the tab being movable relative to the side wall to prevent axial translation of the cap, and wherein the tab is positioned entirely between the proximal and distal walls.

18. The surgical instrument recited in claim 17, wherein the cutout is a first cutout and the tab is a first tab, the side wall defining a second cutout opposite the first cutout, the second cutout defining a second tab.

19. A surgical instrument comprising:
a first portion defining a cavity configured for disposal of a first implant support member, the cavity defining a longitudinal axis; and
a second portion including spaced apart first and second axial slots, the slots each being offset from the longitudinal axis, the second portion being engageable with a second implant support member to orient the second implant support member with the slots such that the second implant support member is connectable with the first implant support member,
wherein the first portion includes a body, the body including opposite proximal and distal walls and a side wall connecting the proximal wall to the distal wall, spaced apart cutouts in the side wall defining spaced apart tabs, the tabs each being movable relative to the side wall to prevent axial translation of the first implant support member.

20. The surgical instrument recited in claim 19, wherein the tabs are each positioned entirely between the proximal and distal walls.

\* \* \* \* \*